United States Patent [19]

Poirier

[11] Patent Number: 4,668,839
[45] Date of Patent: May 26, 1987

[54] PROCESS FOR THE SEPARATION OF SULPHUR COMPOUNDS IN BITUMEN, HEAVY OIL AND SYNTHETIC FUEL DISTILLATES

[75] Inventor: Marc-André Poirier, Ottawa, Canada

[73] Assignee: Her Majesty the Queen in right of Canada, as represented by the Minister of Energy, Mines and Resources Canada, Ottawa, Canada

[21] Appl. No.: 779,067

[22] Filed: Sep. 24, 1985

[30] Foreign Application Priority Data

Jun. 14, 1985 [CA] Canada ................................ 484079

[51] Int. Cl.$^4$ .................... C07C 7/12; C07C 7/135
[52] U.S. Cl. ........................... 585/825; 208/310 R; 436/120
[58] Field of Search ............... 436/120, 91, 140, 161; 422/70; 585/825; 208/310 R, 226, 230, 235

[56] References Cited

U.S. PATENT DOCUMENTS

| 2,509,486 | 5/1950 | Danforth | 208/310 R |
| 2,521,357 | 9/1950 | Furnoy | 585/825 X |
| 2,882,326 | 4/1959 | Jezl | 585/825 |
| 3,150,079 | 9/1964 | Berlin | 585/825 |
| 4,119,404 | 10/1978 | Price | 23/232 E |
| 4,221,569 | 9/1980 | Kebbekus | 23/232 C |
| 4,463,096 | 7/1984 | Hughes | 436/120 X |

Primary Examiner—Glenn Caldarola
Attorney, Agent, or Firm—Finnegan, Henderson, Farabow, Garrett & Dunner

[57] ABSTRACT

A process is described for separating and identifying organic sulphur compounds in petroleum distillates which comprises subjecting an aromatic-containing fraction to chromatography in a dual packed silica gel-alumina column employing pentane-ethyl acetate as a solvent to obtain a sulphur-containing eluate and analyzing the sulphur-containing eluate by gas chromatography and mass spectrometry. The aromatic-containing fraction is usually a naphtha fraction or a light gas oil fraction, with the gas oil fraction being subjected to chromatography on a silica gel column to obtain an aromatic fraction which is then subjected to the chromatography in the above silica gel-alumina column.

5 Claims, No Drawings

PROCESS FOR THE SEPARATION OF SULPHUR COMPOUNDS IN BITUMEN, HEAVY OIL AND SYNTHETIC FUEL DISTILLATES

BACKGROUND OF THE INVENTION

This invention relates to a process for separating and identifying organic sulfur compounds in petroleum distillates.

Studies have been conducted on the effects of increasing the severity of hydrocracking on the compound-type distribution in heavy hydrocarbon feedstocks, such as Athabasca bitumen. It is well known that the sulfur compounds have very undesirable effects on fuel characteristics, engine life and performance. It is, therefore, important to be able to separate and identify the sulfur compounds in terms of determining whether they should be removed, whether they are carcinogenous, or whether they could be used as a chemical or additive.

Various methods have been reported on the separation of organic sulfur compounds from aromatic hydrocarbons in petroleum. Some separation methods are based on liquid exchange chromatography with mercury, zinc or copper salts. Another approach is the chemical conversion of sulphur groups in more polar groups by oxidation and regeneration by reduction to the starting material.

SUMMARY OF THE INVENTION

According to this invention, a process for separating and identifying organic sulphur compounds in petroleum distillates comprises subjecting an aromatic-containing fraction to chromatography in a duel packed silica gel-alumina column to obtain a sulphur-containing eluate and analysing the sulphur-containing eluate by gas chromatography and mass spectrometry.

The petroleum distillate is typically obtained from bitumen, heavy oil or synthetic fuel. The distillate fractions normally utilized are either a naphtha fraction having a boiling point below 200° C. or a light gas oil fraction having a boiling point between 200° and 350° C.

In the case of the light gas oil fraction, this is normally first subjected to a chromatography on a silica gel column to obtain an aromatic fraction which is then subjected to the above described chromatography in the dual packed silica gel-alumina column.

EXAMPLES

A heavy hydrocarbon oil was obtained from the Lloydminster region of Alberta and this was subjected to vacuum distillation to remove the light ends. The resulting feedstock containing 5.05 weight percent sulphur was hydrocracked using a one barrel per day pilot plant hydrocracker. Two products "A" and "B" were obtained under different hydrocracking conditions as set out below in Table 1.

TABLE 1

| Hydrocracking conditions, yields and conversions of the investigated products | | |
|---|---|---|
| | Product "A" | Product "B" |
| Temperature °C. | 420 | 430 |
| Pressure, MPa | 10.44 | 10.44 |
| CHSV | 3 | 3 |
| $H_2$ Consumption, $m^3API/t$ | 17.38 | 15.28 |
| Additive | coal | nil |
| Liquid yield, wt % | 97.28 | 98.30 |
| Pitch Conversion, wt % | 31.3 | 37.5 |

TABLE 1-continued

| Hydrocracking conditions, yields and conversions of the investigated products | | |
|---|---|---|
| | Product "A" | Product "B" |
| Sulphur in Liquid Product, wt % | 4.82 | 4.48 |
| Sulphur Conversion, % | 6.58 | 12.27 |

Gross composition and sulphur distribution in the main fractions of the Lloydminster feedstock and the two hydrocracked products is shown in Tables 2 and 3 below.

TABLE 2

| Gross composition of the liquid feed and hydrocracking products (wt % of total products) | | | |
|---|---|---|---|
| Sample No. | Feedstock | Product "A" | Product "B" |
| Naphtha (i.g.p. - 200° C.) | 1.10 | 2.14 | 4.79 |
| Fraction 200-350° C. | 3.40 | 8.85 | 9.93 |
| Oil and Resins above 350° C. | 69.30 | 66.92 | 63.5 |
| Asphaltenes | 24.93 | 17.80 | 17.70 |
| Benzene insolubles | 0.07 | 0.69 | 0.93 |

Table 3

| Sulphur content in the fractions of the feed and hydrocracking products (wt %) | | | |
|---|---|---|---|
| Sample No. | Feedstock | Product "A" | Product "B" |
| Sulphur in naphtha (i.b.p.-200° C.) | 3.68 | 2.98 | 3.03 |
| Sulphur in fraction (200-275° C.) | 4.54 | 3.92 | 3.87 |
| Sulphur in fraction (275-350° C.) | 4.21 | 3.98 | 3.60 |
| Sulphur in oil and resin Residue above 350° C. | 4.06 | 3.95 | 3.62 |
| Sulphur in asphaltenes | 6.39 | 6.88 | 6.14 |

Hydrocarbon-type distribution is shown in Table 4 below:

TABLE 4

| Hydrocarbon-type distribution in the 200-350° C. fraction of the samples (wt %) | | |
|---|---|---|
| Sample | Saturate | Aromatics |
| Feedstock | 39.7 | 43.0 |
| Hydrocracked product "A" | 46.5 | 41.2 |
| Hydrocracked product "B" | 46.5 | 46.3 |

It will be seen from the above table that there is an increase in the saturates content and a slight increase in the aromatics due to thermal hydrocracking.

The light oil obtained from hydrocracking products "A" and "B" were distilled to separate a naphtha fraction boiling up to 200° C. under atmospheric pressure. The higher boiling range fraction 200°-350° C. was distilled from hydrocracking product "B" under reduced pressure of 1-3 mm Hg.

The following samples were investigated by the separation and identification procedure of the present invention:

1. A 200°-350° C. distillate fraction of the Lloydminster heavy oil prior to hydrocracking.
2. The ibp-200° C. naphtha fraction of the hydrocracked product "A" of the Lloydminster heavy oil.
3. The 200°-350° C. distillate fraction of the hydrocracked product "B" of the Lloydminster heavy oil.

4. A synthetic mixture of 22 pure sulphur compounds and aromatic hydrocarbons, comprising mono- di-and polynuclear aromatics, sulphides and thiophenes. This synthetic mixture is shown in Table 5 below:

TABLE 5

Synthetic mixture of aromatic hydrocarbons and sulphur compounds

| Compound | No. | B.P. (°C.) |
|---|---|---|
| Ethyl phenyl sulphide | 1 | 203 |
| naphthalene | 2 | 218 |
| benzothiophene | 3 | 221 |
| n-amyl sulphide | 4 | 230 |
| n-hexyl sulphide | 5 | 232 |
| azulene | 6 | 255 |
| 1, 3-dimethylnaphthalene | 7 | 263 |
| 3-methylbiphenyl | 8 | 273 |
| acenaphthene | 9 | 279 |
| diphenyl sulphide | 10 | 296 |
| n-heptyl sulphide | 11 | 298 |
| benzyl phenyl sulphide | 12 | 310 |
| 9, 10-dihydroanthracene | 13 | 312 |
| dibenzothiophene | 14 | 332 |
| phenanthrene | 15 | 336 |
| 9-methylanthracene | 16 | 345 |
| n-octyl sulphide | 17 | 352 |
| thianthrene | 18 | 366 |
| 2, 9-dithiadecane | 19 | — |
| dibenzyl sulphide | 20 | m.p. 49° |
| phenyl-$\beta$-phenyl ethyl sulphide | 21 | — |
| phenyl-$\gamma$-phenyl propyl sulphide | 22 | — |

About 2 grams of each of the first three above samples were introduced separately on top of a 4'×0.5" stainless steel column packed with silica gel from Davison Chemical Grade H (100–200 mesh) activated overnight at 240° C. 250 mL Pentane followed by 250 mL benzene were used to elute the saturated hydrocarbons and aromatic hydrocarbons of the samples respectively. The eluents were delivered to the column under pressure using a Lapp Model LS-30 pump at a flow rate of 2.7 mL/min.

EXAMPLE A

The ibp-200° C. naphtha fraction of the hydrocracked product "A" of the Lloydminster oil in an amount of 0.6 g was spiked with about 0.8 mg of azulene and this was chromatographed on 2'×0.5" o.d. stainless steel column dual packed with 19 g silica gel and 25 g alumina. The following sequence of eluents was used:

| Eluent | Volume Used, mL |
|---|---|
| Pentane | 250 |
| Pentane-ethyl acetate (95:5) | 300 |
| Benzene | 250 |

Fractions of eluate (12 mL each) were collected in test tubes on an automatic rotating table. The colored fraction containing the azulene corresponding to the sulphur concentration was examined by gas chromatography-mass spectrometry.

The results obtained are shown in Table 6 below:

TABLE 6

Sulphur compounds identified in the naphtha of hydrocracked Lloydminster oil

| Compound | m/e |
|---|---|
| SULPHIDES | |
| methyl tetrahydrothiophene (23) | 102 |
| methyl tetrahydrothiopyran (24) | 116 |
| dimethyl tetrahydrothiophene (cis/trans) (25) | 116 |

TABLE 6-continued

Sulphur compounds identified in the naphtha of hydrocracked Lloydminster oil

| Compound | m/e |
|---|---|
| ethyl isobutyl sulphide (26) | 118 |
| amyl ethyl sulphide (27) | 132 |
| propyl isobutyl sulphide (28) | 132 |
| n-butyl sulphide (29) | 146 |
| THIOPHENES | |
| benzothiophene (3) | 134 |
| methylbenzothiophene (30) | 148 |
| dimethylbenzothiophene (31) | 162 |
| ethylbenzothiophene (32) | 162 |

The above table shows two series of sulphur compounds, namely benzothiophenes and aromatic sulphides, including cyclic and linear sulphides.

EXAMPLE B

The same procedure as described above in Example A was used in the 200°–350° C. distillate fraction of the hydrocracked product "B" of Lloydminster heavy oil. The results from the gas chromatography and mass spectrometry are shown in Table 7 below:

TABLE 7

Sulphur compounds identified in the light gas oil (200-350° C.) of hydrocracked Lloydminster oil

| Compound | m/e |
|---|---|
| THIOPHENES | |
| trimethylbenzothiophene (33) | 176 |
| dibenzothiophene (14) | 184 |
| diethylbenzothiophene (34) | 190 |
| methyldibenzothiophene (35) | 198 |
| diethyl methylbenzothiophene (36) | 204 |
| dimethyldibenzothiophene (37) | 212 |

The above results show two series of thiophenic sulphur compounds, namely benzothiophene and dibenzothiophene. The mass spectral screening of the fraction examined indicated absence or below the limits of detection of dialkyl and diaryl sulphides.

EXAMPLE C

The same procedure as in Example A was used on the 200°–350° C. distillate fraction from Lloydminster heavy oil prior to hydrocracking. The results of gas chromatography and mass spectrometry are shown in Table 8 below:

TABLE 8

Sulphur compounds identified in the fraction (200-350° C.) of Lloydminster oil

| Compound | m/e |
|---|---|
| THIOPHENES | |
| dimethylbenzothiophen (31) | 162 |
| trimethylbenzothiophene (33) | 176 |
| dibenzothiophene (14) | 184 |
| diethylbenzothiophene (34) | 190 |
| methyldibenzothiophene (35) | 198 |
| diethyl methylbenzothiophene (36) | 204 |

EXAMPLE D

The synthetic mixture of 14 sulphur compounds and 8 aromatics was chromatographed on the dual packed column as described in Example A. The mixture was spiked with azulene which completely eluted with the sulphur compounds, as predetermined by gas chromatography. All the sulphur compounds were eluted in only two fraction (24 mL) of the pentane-ethyl acetate eluate. There was no contamination from other aromatic hydrocarbons except for 9, 10-dihydroanthracene which eluted partly with the sulphur compounds. The mono- and dicyclic aromatics were completely eluted with pentane, while the tricyclic aromatics were retained on the column and were eluted mainly by benzene. The results are shown in Table 9 below.

TABLE 9

Characteristics of aromatic hydrocarbons and sulphur compounds in the chromatographed synthetic mixture

| Compound | No. | B.P. (°C.) | Rt* (min) | Mol. Wt. |
|---|---|---|---|---|
| Ethyl phenyl sulphide | 1 | 203 | 9.35 | 138 |
| naphthalene | 2 | 218 | 11.41 | 128 |
| benzothiophene | 3 | 221 | 13.77 | 134 |
| n-amyl sulphide | 4 | 230 | 11.81 | 174 |
| n-hexyl sulphide | 5 | 232 | 16.75 | 202 |
| azulene | 6 | 255 | 15.25 | 128 |
| 1, 3-dimethylnaphthalene | 7 | 263 | 14.27 | 156 |
| 3-methylbiphenyl | 8 | 273 | 15.05 | 168 |
| acenaphthene | 9 | 279 | 19.29 | 154 |
| diphenyl sulphide | 10 | 296 | 21.16 | 186 |
| n-heptyl sulphide | 11 | 298 | 22.03 | 230 |
| benzyl phenyl sulphide | 12 | 310 | 24.42 | 200 |
| 9, 10-dihydroanthracene | 13 | 312 | 25.00 | 180 |
| dibenzothiophene | 14 | 332 | 30.51 | 184 |
| phenanthrene | 15 | 336 | 29.03 | 178 |
| 9-methylanthracene | 16 | 345 | 33.26 | 191 |
| n-octyl sulphide | 17 | 352 | 26.71 | 258 |
| thianthrene | 18 | 366 | 31.89 | 216 |

TABLE 9-continued

Characteristics of aromatic hydrocarbons and sulphur compounds in the chromatographed synthetic mixture

| Compound | No. | B.P. (°C.) | Rt* (min) | Mol. Wt. |
|---|---|---|---|---|
| 2, 9-dithiadecane | 19 | — | 17.72 | 206 |
| dibenzyl sulphide | 20 | m.p. 49° | 27.33 | 214 |
| phenyl-β-phenyl ethyl sulphide | 21 | — | 28.20 | 214 |
| phenyl-γ-phenyl propyl sulphide | 22 | — | 30.16 | 228 |

*Retention Time

I claim:

1. A process for separating and identifying organic sulphur compounds in petroleum distillates containing a mixture of organic sulphur compounds and aromatic compounds, said aromatic compounds including monocyclic or dicyclic aromatic and polycyclic aromatics, which comprises subjecting said petroleum distillates to chromatography in a dual packed silica gel-alumina column, passing pentane-ethyl acetate through the column to obtain a sulphur-containing eluate and analyzing the sulphur-containing eluate by gas chromatography and mass spectrometry.

2. A process according to claim 1 wherein the petroleum distillate is obtained from bitumen, heavy oil or synthetic fuel.

3. A process according to claim 2 wherein the aromatic-containing fraction is a naphtha fraction having a boiling point below about 200° C.

4. A process according to claim 2 wherein the aromatic-containing fraction is obtained by subjecting a gas oil fraction to silica gel chromatography.

5. A process according to claim 4 wherein the gas oil fraction has a boiling range of 200°–350° C.

* * * * *